(12) United States Patent
Jiao et al.

(10) Patent No.: US 9,716,237 B2
(45) Date of Patent: Jul. 25, 2017

(54) HETEROACENES FOR ORGANIC ELECTRONICS

(71) Applicant: BASF SE, Ludwigshafen (DE)

(72) Inventors: Chongjun Jiao, Singapore (SG); Iori Doi, Singapore (SG); Thomas Weitz, Mannheim (DE); Chao Wu, Mannheim (DE); Wyman Zhao, Singapore (SG); Szehui Chua, Singapore (SG); Stefan Becker, Yongsan-gu (KR); Michael Eustachi, Walldorf (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/120,981

(22) PCT Filed: Feb. 18, 2015

(86) PCT No.: PCT/IB2015/051226
§ 371 (c)(1),
(2) Date: Aug. 23, 2016

(87) PCT Pub. No.: WO2015/128779
PCT Pub. Date: Sep. 3, 2015

(65) Prior Publication Data
US 2016/0365519 A1 Dec. 15, 2016

(30) Foreign Application Priority Data
Feb. 25, 2014 (EP) ..................... 14156504

(51) Int. Cl.
*C07D 495/14* (2006.01)
*H01L 51/00* (2006.01)
*H01L 51/05* (2006.01)

(52) U.S. Cl.
CPC ........ *H01L 51/0074* (2013.01); *C07D 495/14* (2013.01); *H01L 51/0541* (2013.01); *H01L 51/0558* (2013.01)

(58) Field of Classification Search
CPC .................................................. C07D 495/14
See application file for complete search history.

(56) References Cited

U.S. PATENT DOCUMENTS

| 8,642,782 B2 | 2/2014 | Suzuki et al. |
| 2011/0210319 A1 | 9/2011 | Nakano et al. |
| 2011/0220883 A1 | 9/2011 | Nakano et al. |
| 2012/0071668 A1 | 3/2012 | Suzuki et al. |
| 2012/0223276 A1 | 9/2012 | Parham et al. |
| 2013/0245282 A1 | 9/2013 | Takeya et al. |
| 2014/0145175 A1 | 5/2014 | Suzuki et al. |

FOREIGN PATENT DOCUMENTS

WO 2011/057706 A2 5/2011

OTHER PUBLICATIONS

International Search Report Issued Jul. 23, 2015 in PCT/IB2015/051226 Filed Feb. 18, 2018.
International Search Report and Written Opinion issued on Jul. 23, 2015 in PCT/IB2015/051226.
International Preliminary Report on Patentability and Written Opinion issued on Sep. 9, 2016 in PCT/IB2015/051226.

*Primary Examiner* — Noble Jarrell
*Assistant Examiner* — John S Kenyon
(74) *Attorney, Agent, or Firm* — Oblon, McClelland, Maier & Neustadt, L.L.P.

(57) ABSTRACT

The present invention provides compounds of formula 1 wherein $X^1$ and $X^2$ are independently from each other O, S or Se, and an electronic device comprising the compounds as semiconducting material.

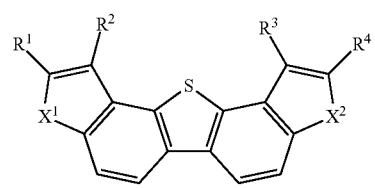

11 Claims, 1 Drawing Sheet

HETEROACENES FOR ORGANIC ELECTRONICS

Organic semiconducting materials can be used in electronic devices such as organic photovoltaic devices (OPVs), organic field-effect transistors (OFETs), organic light emitting diodes (OLEDs), and organic electrochromic devices (ECDs).

For efficient and long lasting performance, it is desirable that the organic semiconducting material-based devices show high charge carrier mobility as well as high stability, in particular towards oxidation by air.

Furthermore, it is desirable that the organic semiconducting materials are compatible with liquid processing techniques such as spin coating as liquid processing techniques are convenient from the point of processability, and thus allow the production of low cost organic semiconducting material-based electronic devices. In addition, liquid processing techniques are also compatible with plastic substrates, and thus allow the production of light weight and mechanically flexible organic semiconducting material-based electronic devices.

The organic semiconducting materials can be either p-type or n-type organic semiconducting materials. It is desirable that both types of organic semiconducting materials are available for the production of electronic devices.

The use of heteroacene compounds containing thieno units as p-type semiconducting materials in electronic devices is known in the art.

US 2011/0220883 discloses alkylated picene as solution-based OFET with a charge carrier mobility of up to 2 cm²/V s.

Shinamura, S.; Osaka, I.; Miyazaki, E.; Nakao, A.; Yamagishi M.; Takeya, J.; Takimiya K. *J. Am. Chem. Soc.* 2011, 133, 5024-5035 describes OFETs comprising one of the following compounds as semiconductor:

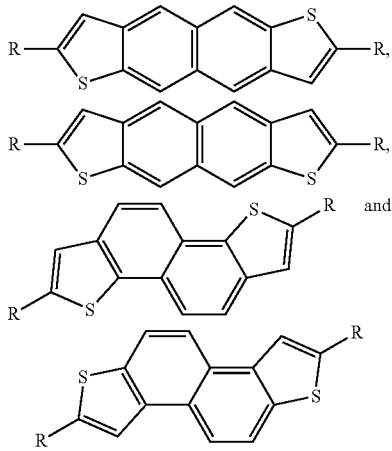

wherein R is H, n-C₈H₁₇ or phenyl.

Gao, J.; Li, R.; Li, L.; Meng, Q.; Jiang, H.; Li, H.; Hu, W. *Adv. Mater.* 2007, 19 (19), 3008-3011 describes OFETs comprising the following compound

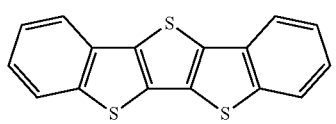 [SMILES: c1ccc2c(c1)sc1c2sc2c3ccccc3sc21]

as semiconductor. The OFET shows a charge carrier mobility of 0.51 cm²/V s and an on/off ratio of 4.5×10⁶.

Miyata, Y.; Yoshikawa, E.; Minari, T.; Tsukagoshi, K.; Yamaguchi, S. *J. Mater. Chem.* 2012, 22, 7715-7717 describes OFETs comprising the following compound

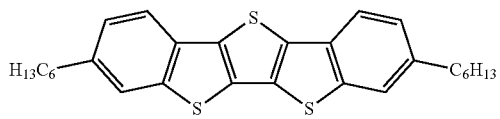

as semiconductor. One of the OFETs shows a charge carrier mobility of 3.1 cm²/V s and an on/off ratio of 10⁵.

Xiao, K; Liu, Y.; Qi, T.; Zhang, W.; Wang, F.; Gao, J.; Qiu, W.; Ma, Y.; Cui, G.; Chen, S.; Zhan, X.; Yu, G.; Qin, J.; Hu, W.; Zhu, D. *J. Am. Chem. Soc.* 2005, 127, 13281-13286 describes OFETs comprising the following compound

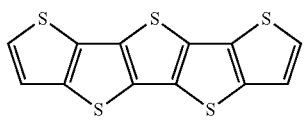

as semiconductor. One of the OFETs shows a charge carrier mobility of 0.045 cm²/V s and an on/off ratio of 10³.

US 2011/0210319 describes organic field effect transistor (OFET) containing the following π-extended S-containing heteroarene compounds

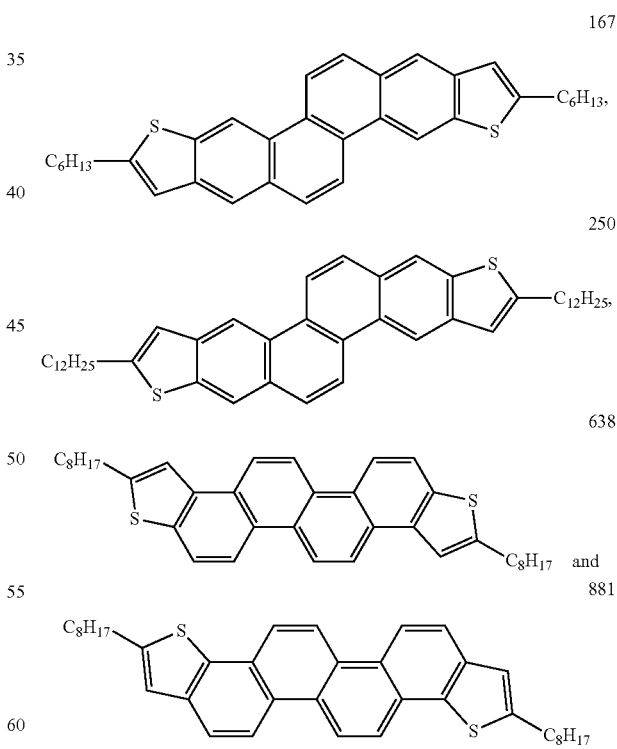

These OFETs show the following charge carrier mobilities: 1.2 (compound 167), 1.8 (compound 250), 2.0 (compound 638), 1.7 (compound 881) cm²/V s, and the following on-off ratios: 2×10⁶ (compound 167), 3×10⁶ (compound 250), 4×10⁵ (compound 638) and 3×10⁶ (compound 881).

US 2013/0245282 describes compounds of following formula

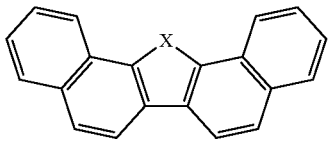

wherein X is O, S or Se, and their use in OFETs.

It was the object of the present invention to provide improved organic semiconducting materials.

This object is solved by the compounds of claim 1, the electronic device of claim 8 and the use of claim 10.

The organic semiconducting materials of the present invention are compounds of formula

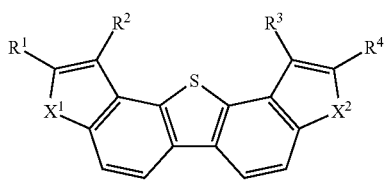

wherein $X^1$ and $X^2$ are independently from each other O, S or Se, and $R^1$, $R^2$, $R^3$ and $R^4$ are independently from each other H, halogen, CN, $NO_2$, $C_{1-30}$-alkyl, $C_{2-30}$-alkenyl, $C_{2-30}$-alkynyl, $C_{6-14}$-aryl or 5 to 14 membered heteroaryl, wherein $C_{1-30}$-alkyl, $C_{2-30}$-alkenyl and $C_{2-30}$-alkynyl can be substituted with one to five substituents independently selected from the group consisting of $C_{6-10}$-aryl, 5 to 10 membered heteroaryl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$; and one or more $CH_2$-groups, but not adjacent $CH_2$-groups, of $C_{1-30}$-alkyl, $C_{2-30}$-alkenyl and $C_{2-30}$-alkynyl can be replaced by O or S, and $C_{6-14}$-aryl and 5 to 14 membered heteroaryl can be substituted with one to five substituents independently selected from the group consisting of $C_{1-20}$-alkyl, $C_{2-20}$-alkenyl, $C_{2-20}$-alkynyl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$, wherein $R^a$ and $R^b$ are independently selected from the group consisting of H, $C_{1-20}$-alkyl, $C_{2-20}$-alkenyl and $C_{2-20}$-alkynyl, $C_{1-20}$-alkyl, $C_{2-20}$-alkenyl and $C_{2-20}$-alkynyl can be substituted with one to five substituents selected from the group consisting of phenyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, and, $C_{6-10}$-aryl and 5 to 10 membered heteroaryl can be substituted with one to five substituents independently selected from the group consisting of $C_{1-10}$-alkyl, $C_{2-10}$-alkenyl, $C_{2-10}$-alkynyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, wherein $R^c$ and $R^d$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$.

Halogen can be F, Cl, Br and I.

$C_{1-10}$-alkyl, $C_{1-20}$-alkyl and $C_{1-30}$-alkyl can be branched or unbranched. Examples of $C_{1-10}$-alkyl are methyl, ethyl, n-propyl, isopropyl, n-butyl, sec-butyl, isobutyl, tert-butyl, n-pentyl, neopentyl, isopentyl, n-(1-ethyl)propyl, n-hexyl, n-heptyl, n-octyl, n-(2-ethyl)hexyl, n-nonyl and n-decyl. Examples of $C_{1-20}$-alkyl are $C_{1-10}$-alkyl and n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$). Examples of $C_{1-30}$-alkyl are $C_{1-20}$-alkyl and n-docosyl ($C_{22}$), n-tetracosyl ($C_{24}$), n-hexacosyl ($C_{26}$), n-octacosyl ($C_{28}$) and n-triacontyl ($C_{30}$).

$C_{2-10}$-alkenyl, $C_{2-20}$-alkenyl and $C_{2-30}$-alkenyl can be branched or unbranched. Examples of $C_{1-20}$-alkenyl are vinyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl and docenyl. Examples of $C_{2-20}$-alkenyl are $C_{2-10}$-alkenyl and linoleyl ($C_{18}$), linolenyl ($C_{18}$), oleyl ($C_{18}$), and arachidonyl ($C_{20}$). Examples of $C_{2-30}$-alkenyl are $C_{2-20}$-alkenyl and erucyl ($C_{22}$).

$C_{2-10}$-alkynyl, $C_{2-20}$-alkynyl and $C_{2-30}$-alkynyl can be branched or unbranched. Examples of $C_{2-10}$-alkynyl are ethynyl, 2-propynyl, 2-butynyl, 3-butynyl, pentynyl, hexynyl, heptynyl, octynyl, nonynyl and decynyl. Examples of $C_{2-20}$-alkynyl and $C_{2-30}$-alkenyl are undecynyl, dodecynyl, undecynyl, dodecynyl, tridecynyl, tetradecynyl, pentadecynyl, hexadecynyl, heptadecynyl, octadecynyl, nonadecynyl and icosynyl ($C_{20}$).

Examples of $C_{6-10}$-aryl are phenyl, naphthyl, anthracenyl and phenantrenyl.

Examples of $C_{6-14}$-aryl are $C_{6-10}$-aryl and tetracenyl and chrysenyl.

Examples of 5 to 10 membered heteroaryl are

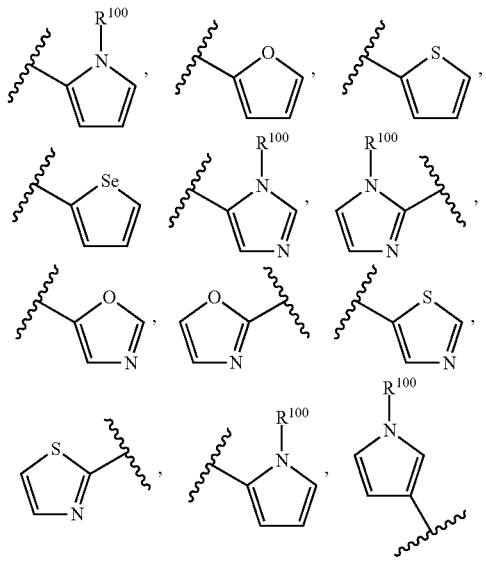

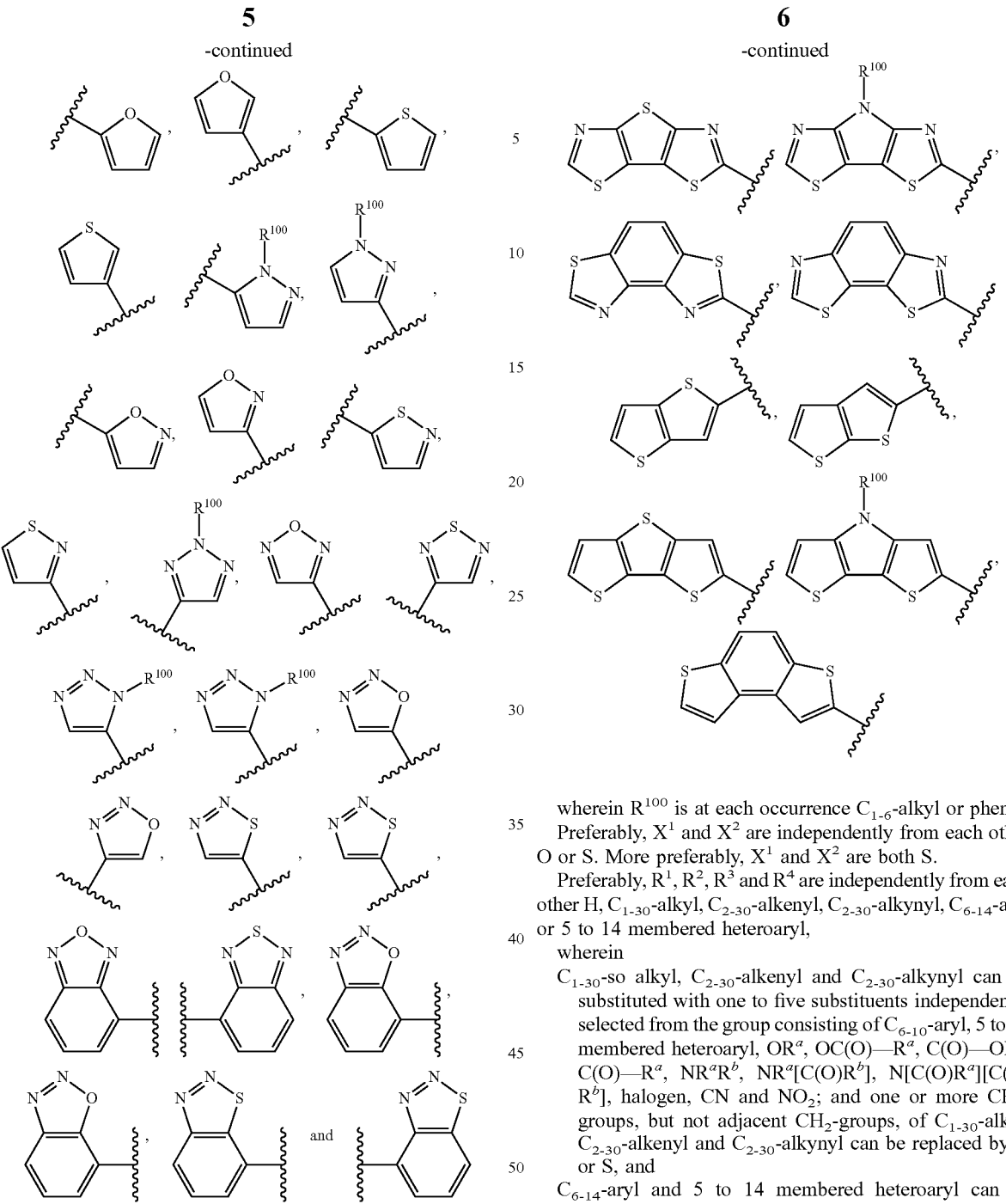

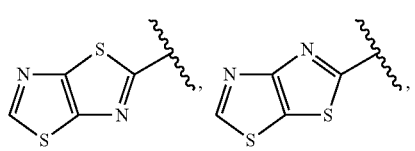

wherein $R^{100}$ is at each occurrence $C_{1-6}$-alkyl or phenyl.

Examples of 5 to 14 membered heteroaryl are the examples given for the 5 to 10 membered heteroaryl and wherein $R^{100}$ is at each occurrence $C_{1-6}$-alkyl or phenyl.

Preferably, $X^1$ and $X^2$ are independently from each other O or S. More preferably, $X^1$ and $X^2$ are both S.

Preferably, $R^1$, $R^2$, $R^3$ and $R^4$ are independently from each other H, $C_{1-30}$-alkyl, $C_{2-30}$-alkenyl, $C_{2-30}$-alkynyl, $C_{6-14}$-aryl or 5 to 14 membered heteroaryl, wherein $C_{1-30}$-so alkyl, $C_{2-30}$-alkenyl and $C_{2-30}$-alkynyl can be substituted with one to five substituents independently selected from the group consisting of $C_{6-10}$-aryl, 5 to 10 membered heteroaryl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$; and one or more $CH_2$-groups, but not adjacent $CH_2$-groups, of $C_{1-30}$-alkyl, $C_{2-30}$-alkenyl and $C_{2-30}$-alkynyl can be replaced by O or S, and $C_{6-14}$-aryl and 5 to 14 membered heteroaryl can be substituted with one to five substituents independently selected from the group consisting of $C_{1-20}$-alkyl, $C_{2-20}$-alkenyl, $C_{2-20}$-alkynyl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$, wherein $R^a$ and $R^b$ are independently selected from the group consisting of H, $C_{1-20}$-alkyl, $C_{2-20}$-alkenyl and $C_{2-20}$-alkynyl, $C_{1-20}$-alkyl, $C_{2-20}$-alkenyl and $C_{2-20}$-alkynyl can be substituted with one to five substituents selected from the group consisting of phenyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, and, $C_{6-10}$-aryl and 5 to 10 membered heteroaryl can be substituted with one to five substituents independently selected from the group consisting of $C_{1-10}$-alkyl, $C_{2-10}$-alkenyl, $C_{2-10}$-alkynyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, wherein $R^c$ and $R^d$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$.

More preferably, $R^1$, $R^2$, $R^3$ and $R^4$ are independently from each other H, $C_{1-30}$-alkyl, $C_{6-14}$-aryl or 5 to 14 membered heteroaryl, wherein $C_{1-30}$-alkyl can be substituted with one to five substituents independently selected from the group consisting of $C_{6-10}$-aryl, 5 to 10 membered heteroaryl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$; and one or more $CH_2$-groups, but not adjacent $CH_2$-groups, of $C_{1-30}$-alkyl can be replaced by O or S, and $C_{6-14}$-aryl and 5 to 14 membered heteroaryl can be substituted with one to five substituents independently selected from the group consisting of $C_{1-20}$-alkyl, $C_{2-20}$-alkenyl, $C_{2-20}$-alkynyl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$, wherein $R^a$ and $R^b$ are independently selected from the group consisting of H, $C_{1-20}$-alkyl, $C_{2-20}$-alkenyl and $C_{2-20}$-alkynyl, $C_{1-20}$-alkyl, $C_{2-20}$-alkenyl and $C_{2-20}$-alkynyl can be substituted with one to five substituents selected from the group consisting of phenyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, and, $C_{6-10}$-aryl and 5 to 10 membered heteroaryl can be substituted with one to five substituents independently selected from the group consisting of $C_{1-10}$-alkyl, $C_{2-10}$-alkenyl, $C_{2-10}$-alkynyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, wherein $R^c$ and $R^d$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$.

Even more preferably, $R^2$ and $R^3$ are H, and $R^1$ and $R^4$ are independently from each other H or $C_{1-30}$-alkyl, wherein $C_{1-30}$-alkyl can be substituted with one to five substituents independently selected from the group consisting of $C_{6-10}$-aryl, 5 to 10 membered heteroaryl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$; and one or more $CH_2$-groups, but not adjacent $CH_2$-groups, of $C_{1-30}$-alkyl can be replaced by O or S, wherein $R^a$ and $R^b$ are independently selected from the group consisting of H, $C_{1-20}$-alkyl, $C_{2-20}$-alkenyl and $C_{2-20}$-alkynyl, $C_{1-20}$-alkyl, $C_{2-20}$-alkenyl and $C_{2-20}$-alkynyl can be substituted with one to five substituents selected from the group consisting of phenyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, and, $C_{6-10}$-aryl and 5 to 10 membered heteroaryl can be substituted with one to five substituents independently selected from the group consisting of $C_{1-10}$-alkyl, $C_{2-10}$-alkenyl, $C_{2-10}$-alkynyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, wherein $R^c$ and $R^d$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$.

Most preferably, $R^2$ and $R^3$ are H, and $R^1$ and $R^4$ are independently from each other H or $C_{1-30}$-alkyl.

Preferred are compounds of formula

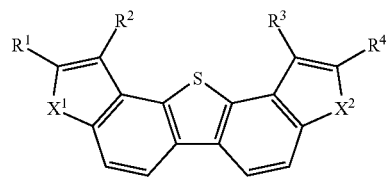

wherein $X^1$ and $X^2$ are independently from each other O or S, and $R^1$, $R^2$, $R^3$ and $R^4$ are independently from each other H, $C_{1-30}$-alkyl, $C_{2-30}$-alkenyl, $C_{2-30}$-alkynyl, $C_{6-14}$-aryl or 5 to 14 membered heteroaryl, wherein $C_{1-30}$-alkyl, $C_{2-30}$-alkenyl and $C_{2-30}$-alkynyl can be substituted with one to five substituents independently selected from the group consisting of $C_{6-10}$-aryl, 5 to 10 membered heteroaryl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$; and one or more $CH_2$-groups, but not adjacent $CH_2$-groups, of $C_{1-30}$-alkyl, $C_{2-30}$-alkenyl and $C_{2-30}$-alkynyl can be replaced by O or S, and $C_{6-14}$-aryl and 5 to 14 membered heteroaryl can be substituted with one to five substituents independently selected from the group consisting of $C_{1-20}$-alkyl, $C_{2-20}$-alkenyl, $C_{2-20}$-alkynyl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$, wherein $R^a$ and $R^b$ are independently selected from the group consisting of H, $C_{1-20}$-alkyl, $C_{2-20}$-alkenyl and $C_{2-20}$-alkynyl, $C_{1-20}$-alkyl, $C_{2-20}$-alkenyl and $C_{2-20}$-alkynyl can be substituted with one to five substituents selected from the group consisting of phenyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, and, $C_{6-10}$-aryl and 5 to 10 membered heteroaryl can be substituted with one to five substituents independently selected from the group consisting of $C_{1-10}$-alkyl, $C_{2-10}$-alkenyl, $C_{2-10}$-alkynyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, wherein $R^c$ and $R^d$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$.

More preferred are compounds of formula

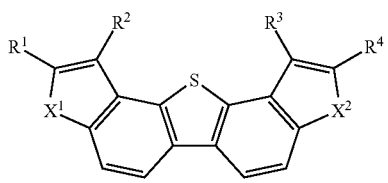

wherein $X^1$ and $X^2$ are independently from each other O or S, and $R^1$, $R^2$, $R^3$ and $R^4$ are independently from each other H, $C_{1-30}$-alkyl, $C_{6-14}$-aryl or 5 to 14 membered heteroaryl, wherein $C_{1-30}$-alkyl can be substituted with one to five substituents independently selected from the group consisting of $C_{6-10}$-aryl, 5 to 10 membered heteroaryl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$; and one or more $CH_2$-groups, but not adjacent $CH_2$-groups, of $C_{1-30}$-alkyl can be replaced by O or S, and $C_{6-14}$-aryl and 5 to 14 membered heteroaryl can be substituted with one to five substituents independently selected from the group consisting of $C_{1-20}$-alkyl, $C_{2-20}$-alkenyl, $C_{2-20}$-alkynyl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$, wherein $R^a$ and $R^b$ are independently selected from the group consisting of H, $C_{1-20}$-alkyl, $C_{2-20}$-alkenyl and $C_{2-20}$-alkynyl, $C_{1-20}$-alkyl, $C_{2-20}$-alkenyl and $C_{2-20}$-alkynyl can be substituted with one to five substituents selected from the group consisting of phenyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, and, $C_{6-10}$-aryl and 5 to 10 membered heteroaryl can be substituted with one to five substituents independently selected from the group consisting of $C_{1-10}$-alkyl, $C_{2-10}$-alkenyl, $C_{2-10}$-alkynyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, wherein $R^c$ and $R^d$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$.

Even more preferred are compounds of formula

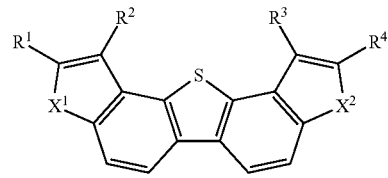

wherein $X^1$ and $X^2$ are both S, and $R^2$ and $R^3$ are H, and $R^1$ and $R^4$ are independently from each other H or $C_{1-30}$-alkyl, wherein $C_{1-30}$-alkyl can be substituted with one to five substituents independently selected from the group consisting of $C_{6-10}$-aryl, 5 to 10 membered heteroaryl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$; and one or more $CH_2$-groups, but not adjacent $CH_2$-groups, of $C_{1-30}$-alkyl can be replaced by O or S, wherein $R^a$ and $R^b$ are independently selected from the group consisting of H, $C_{1-20}$-alkyl, $C_{2-20}$-alkenyl and $C_{2-20}$-alkynyl, $C_{1-20}$-alkyl, $C_{2-20}$-alkenyl and $C_{2-20}$-alkynyl can be substituted with one to five substituents selected from the group consisting of phenyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, and, $C_{6-10}$-aryl and 5 to 10 membered heteroaryl can be substituted with one to five substituents independently selected from the group consisting of $C_{1-10}$-alkyl, $C_{2-10}$-alkenyl, $C_{2-10}$-alkynyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, wherein $R^c$ and $R^d$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$.

Most preferred are compounds of formula

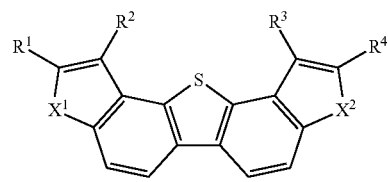

wherein
X¹ and X² are both S, and
R² and R³ are H, and R¹ and R⁴ are independently from each other H or $C_{1-30}$-alkyl.

In particular preferred are the following compounds

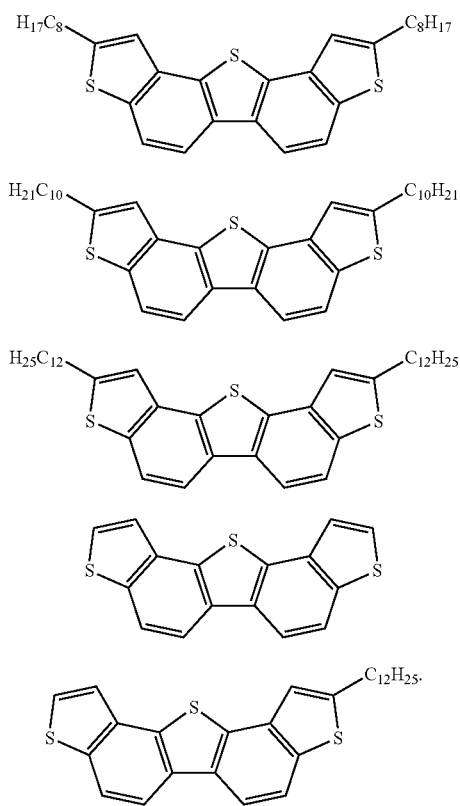

1a

1b

1c

1d

1e and

The compounds of formula 1 can be prepared by methods known in the art.

For example, the compound of formula 1 can be prepared from a compound of formula 3 as outlined below:

wherein
X¹ and X² are independently from each other O, S or Se, and

R¹, R², R³ and R⁴ are independently from each other H, halogen, CN, NO₂, $C_{1-30}$-alkyl, $C_{2-30}$-alkenyl, $C_{2-30}$-alkynyl, $C_{6-14}$-aryl or 5 to 14 membered heteroaryl, wherein $C_{1-30}$-alkyl, $C_{2-30}$-alkenyl and $C_{2-30}$-alkynyl can be substituted with one to five substituents independently selected from the group consisting of $C_{6-10}$-aryl, 5 to 10 membered heteroaryl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and NO₂; and one or more $CH_2$-groups, but not adjacent $CH_2$-groups, of $C_{1-30}$-alkyl, $C_{2-30}$-alkenyl and $C_{2-30}$-alkynyl can be replaced by O or S, and $C_{6-14}$-aryl and 5 to 14 membered heteroaryl can be substituted with one to five substituents independently selected from the group consisting of $C_{1-20}$-alkyl, $C_{2-20}$-alkenyl, $C_{2-20}$-alkynyl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and NO₂, wherein $R^a$ and $R^b$ are independently selected from the group consisting of H, $C_{1-20}$-alkyl, $C_{2-20}$-alkenyl and $C_{2-20}$-alkynyl, $C_{1-20}$-alkyl, $C_{2-20}$-alkenyl and $C_{2-20}$-alkynyl can be substituted with one to five substituents selected from the group consisting of phenyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and NO₂, and, $C_{6-10}$-aryl and 5 to 10 membered heteroaryl can be substituted with one to five substituents independently selected from the group consisting of $C_{1-10}$-alkyl, $C_{2-10}$-alkenyl, $C_{2-10}$-alkynyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and NO₂, wherein $R^c$ and $R^d$ are independently selected from the group consisting of H, $C_{1-10}$-alkyl, $C_{2-10}$-alkenyl and $C_{2-10}$-alkynyl,

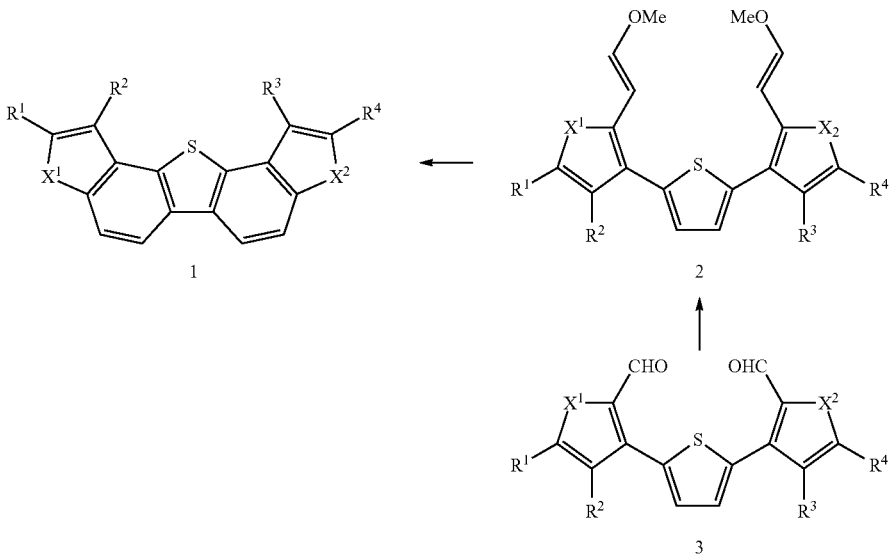

wherein
  $C_{1-10}$-alkyl, $C_{2-10}$-alkenyl and $C_{2-10}$-alkynyl can be substituted with one to five substituents selected from the group consisting of halogen, CN and $NO_2$.

The compound of formula 3 can be treated with (methoxymethyl)triphenylphosphonium chloride in the presence of a base such as KOtBu in order to obtain the compound of formula 2. The compound of formula 2 is usually obtained together with isomers of the compound of formula 2. The reaction is usually performed in a suitable solvent such as ether, for example tetrahydrofuran or diethylether. The reaction is usually performed at low temperatures, for example between −80 and −15° C., preferably between −60 and −30° C.

The compound of formula 2 (usually in a mixture with the isomers of the compound of formula 2) can be treated with a strong acid such as methanesulfonic acid in order to obtain the compound of formula 1. The reaction is usually performed in an inert organic solvent such as dichloromethane. The reaction is usually performed at temperatures between −25 and 10° C., preferably at 0° C.

The compound of formula 3 can be prepared from a compound of formula 8 as outlined below:

$(O)R^b$], $N[C(O)R^a][C(O)R^b]$, halogen, CN and $NO_2$; and one or more $CH_2$-groups, but not adjacent $CH_2$-groups, of $C_{1-30}$-alkyl, $C_{2-30}$-alkenyl and $C_{2-30}$-alkynyl can be replaced by O or S, and $C_{6-14}$-aryl and 5 to 14 membered heteroaryl can be substituted with one to five substituents independently selected from the group consisting of $C_{1-20}$-alkyl, $C_{2-20}$-alkenyl, $C_{2-20}$-alkynyl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$, wherein
  $R^a$ and $R^b$ are independently selected from the group consisting of H, $C_{1-20}$-alkyl, $C_{2-20}$-alkenyl and $C_{2-20}$-alkynyl,
  $C_{1-20}$-alkyl, $C_{2-20}$-alkenyl and $C_{2-20}$-alkynyl can be substituted with one to five substituents selected from the group consisting of phenyl, $OR^c$, $OC(O)$—$R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, and,
  $C_{6-10}$-aryl and 5 to 10 membered heteroaryl can be substituted with one to five substituents independently selected from the group consisting of $C_{1-10}$-alkyl, $C_{2-10}$-alkenyl, $C_{2-10}$-alkynyl, $OR^c$, $OC(O)$—

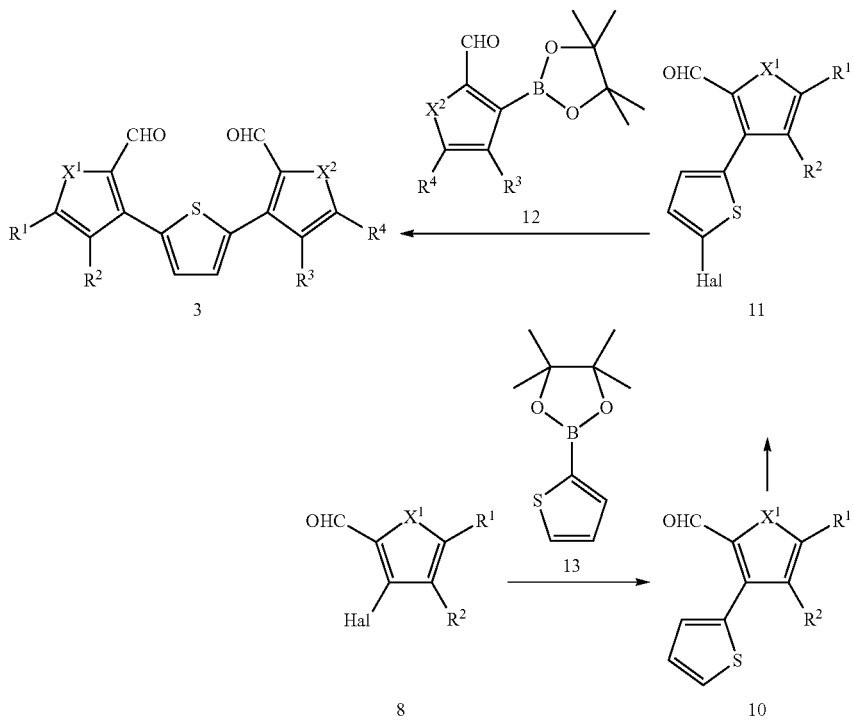

wherein
  $X^1$ and $X^2$ are independently from each other O, S or Se, and
  $R^1$, $R^2$, $R^3$ and $R^4$ are independently from each other H, halogen, CN, $NO_2$, $C_{1-30}$-alkyl, $C_{2-30}$-alkenyl, $C_{2-30}$-alkynyl, $C_{6-14}$-aryl or 5 to 14 membered heteroaryl,
  wherein
    $C_{1-30}$-alkyl, $C_{2-30}$-alkenyl and $C_{2-30}$-alkynyl can be substituted with one to five substituents independently selected from the group consisting of $C_{6-10}$-aryl, 5 to 10 membered heteroaryl, $OR^a$, $OC(O)$—$R^a$, $C(O)$—$OR^a$, $C(O)$—$R^a$, $NR^aR^b$, $NR^a[C$ $R^c$, $C(O)$—$OR^c$, $C(O)$—$R^c$, $NR^cR^d$, $NR^c[C(O)R^d]$, $N[C(O)R^c][C(O)R^d]$, halogen, CN and $NO_2$, wherein
  $R^c$ and $R^d$ are independently selected from the group consisting of H, $C_{1-10}$-alkyl, $C_{2-10}$-alkenyl and $C_{2-10}$-alkynyl,
  wherein
    $C_{1-10}$-alkyl, $C_{2-10}$-alkenyl and $C_{2-10}$-alkynyl can be substituted with one to five substituents selected from the group consisting of halogen, CN and $NO_2$.

A mixture of the compounds of formula 8 and 13 can be treated with a palladium catalyst such as $Pd(P^tBu_3)_2$ in the presence of a base such as CsF in order to obtain the compound of formula 10. The reaction is usually performed in suitable solvent or solvent mixture such as a mixture of 1,4-dioxane and water. The reaction is usually performed at temperatures between 15 and 120° C., preferably between 50 and 100° C.

The compound of formula 10 can be treated with a suitable halogenating agent such as N-bromosuccinimide in order to obtain the compound of formula 11. The reaction is usually performed in suitable solvent or solvent mixture such as dichloromethane. The reaction is usually performed at temperatures between −25 and 5° C., preferably at 0° C.

A mixture of the compounds of formula 11 and 12 can be treated with a palladium catalyst such as $Pd(P^tBu_3)_2$ in the presence of a base such as CsF in order to obtain the compound of formula 3. The reaction is usually performed in suitable solvent or solvent mixture such as a mixture of 1,4-dioxane and water. The reaction is usually performed at temperatures between 15 and 120° C., preferably between 50 and 100° C.

Symmetric compounds of formula 3 can be prepared as outlined below:

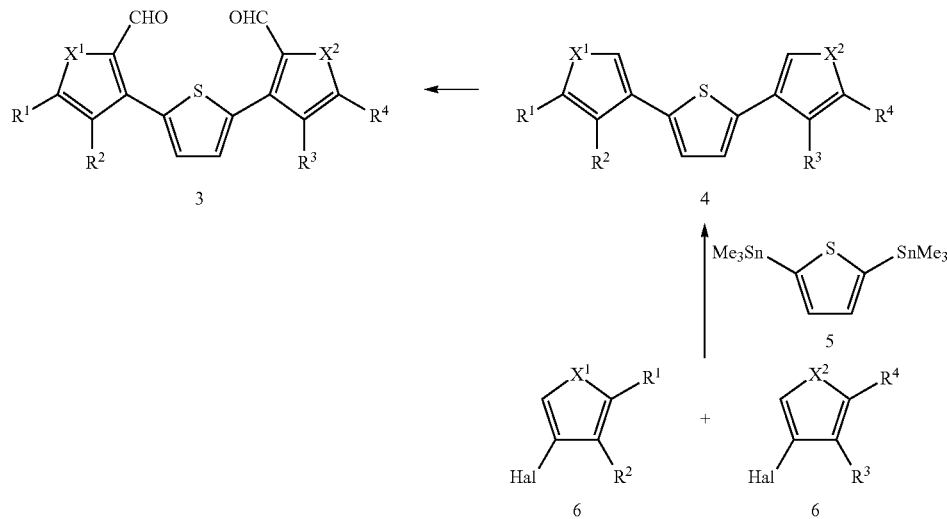

wherein $X^1$ and $X^2$ are identical and are O, S or Se, $R^1$ and $R^2$ are independently from each other H, halogen, CN, $NO_2$, $C_{1-30}$-alkyl, $C_{2-30}$-alkenyl, $C_{2-30}$-alkynyl, $C_{6-14}$-aryl or 5 to 14 membered heteroaryl, wherein $C_{1-30}$-alkyl, $C_{2-30}$-alkenyl and $C_{2-30}$-alkynyl can be substituted with one to five substituents independently selected from the group consisting of $C_{6-10}$-aryl, 5 to 10 membered heteroaryl, $OR^a$, $OC(O)-R^a$, $C(O)-OR^a$, $C(O)-R^a$, $NR^aR^b$, $NR^a[C(O)R^b]$, $N[C(O)R^a][C(O)R^b]$, halogen, CN and $NO_2$; and one or more $CH_2$-groups, but not adjacent $CH_2$-groups, of $C_{1-30}$-alkyl, $C_{2-30}$-alkenyl and $C_{2-30}$-alkynyl can be replaced by O or S, and $C_{6-14}$-aryl and 5 to 14 membered heteroaryl can be substituted with one to five substituents independently selected from the group consisting of $C_{1-20}$-alkyl, $C_{2-20}$-alkenyl, $C_{2-20}$-alkynyl, $OR^a$, $OC(O)-R^a$, $C(O)-OR^a$, $C(O)-R^a$, $NR^aR^b$, $NR^a[C(O)R^b]$, $N[C(O)R^a][C(O)R^b]$, halogen, CN and $NO_2$, wherein $R^a$ and $R^b$ are independently selected from the group consisting of H, $C_{1-20}$-alkyl, $C_{2-20}$-alkenyl and $C_{2-20}$-alkynyl, $C_{1-20}$-alkyl, $C_{2-20}$-alkenyl and $C_{2-20}$-alkynyl can be substituted with one to five substituents selected from the group consisting of phenyl, $OR^c$, $OC(O)-R^c$, $C(O)-OR^c$, $C(O)-R^c$, $NR^cR^d$, $NR^c[C(O)R^d]$, $N[C(O)R^c][C(O)R^d]$, halogen, CN and $NO_2$, and, $C_{6-10}$-aryl and 5 to 10 membered heteroaryl can be substituted with one to five substituents independently selected from the group consisting of $C_{1-10}$-alkyl, $C_{2-10}$-alkenyl, $C_{2-10}$-alkynyl, $OR^c$, $OC(O)-R^c$, $C(O)-OR^c$, $C(O)-R^c$, $NR^cR^d$, $NR^c[C(O)R^d]$, $N[C(O)R^c][C(O)R^d]$, halogen, CN and $NO_2$, wherein $R^c$ and $R^d$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$, $R^4=R^1$, and $R^3=R^2$.

A mixture of compound 5 and compound 6 can be treated with a palladium catalyst, for example $Pd(PPh_3)_4$ in order to obtain a compound of formula 4. The reaction is usually performed in suitable solvent or solvent mixture such as dimethylformamide. The reaction is usually performed at temperatures between 30 and 120° C., preferably between 70 and 110° C.

The compound 4 can be treated with dimethylformamide in the presence of $POCl_3$ in order to obtain compound 3. The reaction is usually performed in suitable solvent or solvent mixture such as dichloromethane. The reaction is usually performed at temperatures between −25 and 60° C.

Symmetric compounds of formula 3 can also be prepared as outlined below:

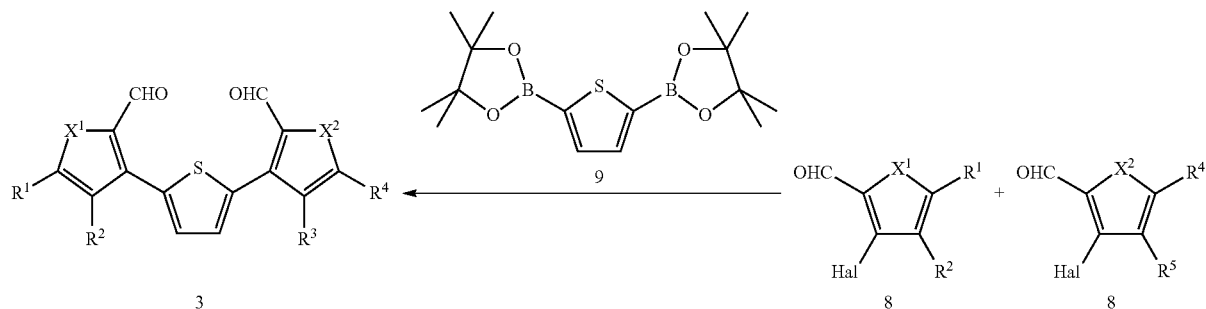

wherein

X$^1$ and X$^2$ are identical and are O, S or Se,

R$^1$ and R$^2$ are independently from each other H, halogen, CN, NO$_2$, C$_{1-30}$-alkyl, C$_{2-30}$-alkenyl, C$_{2-30}$-alkynyl, C$_{6-14}$-aryl or 5 to 14 membered heteroaryl, wherein C$_{1-30}$-alkyl, C$_{2-30}$-alkenyl and C$_{2-30}$-alkynyl can be substituted with one to five substituents independently selected from the group consisting of C$_{6-10}$-aryl, 5 to 10 membered heteroaryl, OR$^a$, OC(O)—R$^a$, C(O)—OR$^a$, C(O)—R$^a$, NR$^a$R$^b$, NR$^a$[C(O)R$^b$], N[C(O)R$^a$][C(O)R$^b$], halogen, CN and NO$_2$; and one or more CH$_2$-groups, but not adjacent CH$_2$-groups, of C$_{1-30}$-alkyl, C$_{2-30}$-alkenyl and C$_{2-30}$-alkynyl can be replaced by O or S, and C$_{6-14}$-aryl and 5 to 14 membered heteroaryl can be substituted with one to five substituents independently selected from the group consisting of C$_{1-20}$-alkyl, C$_{2-20}$-alkenyl, C$_{2-20}$-alkynyl, OR$^a$, OC(O)—R$^a$, C(O)—OR$^a$, C(O)—R$^a$, NR$^a$R$^b$, NR$^a$[C(O)R$^b$], N[C(O)R$^a$][C(O)R$^b$], halogen, CN and NO$_2$, wherein R$^a$ and R$^b$ are independently selected from the group consisting of H, C$_{1-20}$-alkyl, C$_{2-20}$-alkenyl and C$_{2-20}$-alkynyl, C$_{1-20}$-alkyl, C$_{2-20}$-alkenyl and C$_{2-20}$-alkynyl can be substituted with one to five substituents selected from the group consisting of phenyl, OR$^c$, OC(O)—R$^c$, C(O)—OR$^c$, C(O)—R$^c$, NR$^c$R$^d$, NR$^c$[C(O)R$^d$], N[C(O)R$^c$][C(O)R$^d$], halogen, CN and NO$_2$, and, C$_{6-10}$-aryl and 5 to 10 membered heteroaryl can be substituted with one to five substituents independently selected from the group consisting of C$_{1-10}$-alkyl, C$_{2-10}$-alkenyl, C$_{2-10}$-alkynyl, OR$^c$, OC(O)—R$^c$, C(O)—OR$^c$, C(O)—R$^c$, NR$^c$R$^d$, NR$^c$[C(O)R$^d$], N[C(O)R$^c$][C(O)R$^d$], halogen, CN and NO$_2$, wherein R$^c$ and R$^d$ are independently selected from the group consisting of H, C$_{1-10}$-alkyl, C$_{2-10}$-alkenyl and C$_{2-10}$-alkynyl, wherein C$_{1-10}$-alkyl, C$_{2-10}$-alkenyl and C$_{2-10}$-alkynyl can be substituted with one to five substituents selected from the group consisting of halogen, CN and NO$_2$, R$^4$=R$^1$, and

R$^3$=R$^2$.

A mixture of the compound of formula 8 and the compound of formula 9 can be treated a palladium catalyst such as Pd(PtBu$_3$)$_2$ in the presence of a base such as CsF in order to obtain the compound of formula 3. The reaction is usually performed in suitable solvent or solvent mixture such as a mixture of 1,4-dioxane and water. The reaction is usually performed at temperatures between 15 and 120° C., preferably between 50 and 100° C.

The starting compounds of formula 6 and 8 can be prepared as outlined below:

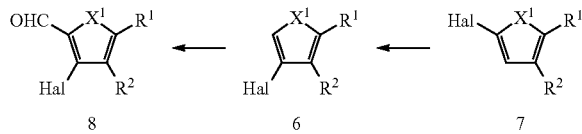

wherein

X$_1$ is O, S or Se,

R$^1$ and R$^2$ are independently from each other H, halogen, CN, NO$_2$, C$_{1-30}$-alkyl, C$_{2-30}$-alkenyl, C$_{2-30}$-alkynyl, C$_{6-14}$-aryl or 5 to 14 membered heteroaryl, wherein C$_{1-30}$-alkyl, C$_{2-30}$-alkenyl and C$_{2-30}$-alkynyl can be substituted with one to five substituents independently selected from the group consisting of C$_{6-10}$-aryl, 5 to 10 membered heteroaryl, OR$^a$, OC(O)—R$^a$, C(O)—OR$^a$, C(O)—R$^a$, NR$^a$R$^b$, NR$^a$[C(O)R$^b$], N[C(O)R$^a$][C(O)R$^b$], halogen, CN and NO$_2$; and one or more CH$_2$-groups, but not adjacent CH$_2$-groups, of C$_{1-30}$-alkyl, C$_{2-30}$-alkenyl and C$_{2-30}$-alkynyl can be replaced by O or S, and C$_{6-14}$-aryl and 5 to 14 membered heteroaryl can be substituted with one to five substituents independently selected from the group consisting of C$_{1-20}$-alkyl, C$_{2-20}$-alkenyl, C$_{2-20}$-alkynyl, OR$^a$, OC(O)—R$^a$, C(O)—OR$^a$, C(O)—R$^a$, NR$^a$R$^b$, NR$^a$[C(O)R$^b$], N[C(O)R$^a$][C(O)R$^b$], halogen, CN and NO$_2$, wherein R$^a$ and R$^b$ are independently selected from the group consisting of H, C$_{1-20}$-alkyl, C$_{2-20}$-alkenyl and C$_{2-20}$-alkynyl, C$_{1-20}$-alkyl, C$_{2-20}$-alkenyl and C$_{2-20}$-alkynyl can be substituted with one to five substituents selected from the group consisting of phenyl, OR$^c$, OC(O)—R$^c$, C(O)—OR$^c$, C(O)—R$^c$, NR$^c$R$^d$, NR$^c$[C(O)R$^d$], N[C(O)R$^c$][C(O)R$^d$], halogen, CN and NO$_2$, and, C$_{6-10}$-aryl and 5 to 10 membered heteroaryl can be substituted with one to five substituents independently selected from the group consisting of C$_{1-10}$-alkyl, C$_{2-10}$-alkenyl, C$_{2-10}$-alkynyl, OR$^c$, OC(O)—R$^c$, C(O)—OR$^c$, C(O)—R$^c$, NR$^c$R$^d$, NR$^c$[C(O)R$^d$], N[C(O)R$^c$][C(O)R$^d$], halogen, CN and NO$_2$, wherein R$^c$ and R$^d$ are independently selected from the group consisting of H, C$_{1-10}$-alkyl, C$_{2-10}$-alkenyl and C$_{2-10}$-alkynyl, wherein C$_{1-10}$-alkyl, C$_{2-10}$-alkenyl and C$_{2-10}$-alkynyl can be substituted with one to five substituents selected from the group consisting of halogen, CN and NO$_2$.

The compound of formula 7 can be treated with a strong base such as lithiumdiisopropylamide in order to obtain a compound of formula 6. The reaction is usually performed in suitable solvent or solvent mixture such as tetrahydrofuran. The reaction is usually performed at temperatures between −25 and 50° C., preferably between −5 and 30° C.

The compound of formula 6 can be treated with a formylating agent such as 1-formyl-piperidine in the presence of a strong base such as lithium diisopropylamide in order to obtain a compound of formula 8. The reaction is usually performed in suitable solvent or solvent mixture such as tetrahydrofuran. The reaction is usually performed at temperatures between −25 and 50° C., preferably between −5 and 30° C.

Also part of the present invention is an electronic device comprising the compound of formula 1. Preferably, the electronic device is an organic field effect transistor (OFET).

Usually, an organic field effect transistor comprises a dielectric layer, a semiconducting layer and a substrate. In addition, an organic field effect transistor usually comprises a gate electrode and source/drain electrodes.

Preferably, the semiconducting layer comprises the compound of formula 1. The semiconducting layer can have a thickness of 5 to 500 nm, preferably of 10 to 100 nm, more preferably of 20 to 50 nm.

The dielectric layer comprises a dielectric material. The dielectric material can be silicon dioxide or aluminium oxide, or, an organic polymer such as polystyrene (PS), poly(methylmethacrylate) (PMMA), poly(4-vinylphenol) (PVP), poly(vinyl alcohol) (PVA), benzocyclobutene (BCB), or polyimide (PI). The dielectric layer can have a thickness of 10 to 2000 nm, preferably of 50 to 1000 nm, more preferably of 100 to 800 nm.

The dielectric layer can in addition to the dielectric material comprise a self-assembled monolayer of organic silane derivates or organic phosphoric acid derivatives. An example of an organic silane derivative is octyltrichlorosilane. An examples of an organic phosphoric acid derivative is octyldecylphosphoric acid. The self-assembled monolayer comprised in the dielectric layer is usually in contact with the semiconducting layer.

The source/drain electrodes can be made from any suitable source/drain material, for example gold (Au) or tantalum (Ta). The source/drain electrodes can have a thickness of 1 to 100 nm, preferably from 20 to 70 nm.

The gate electrode can be made from any suitable gate material such as highly doped silicon, aluminium (Al), tungsten (W), indium tin oxide, gold (Au) and/or tantalum (Ta). The gate electrode can have a thickness of 1 to 200 nm, preferably from 5 to 100 nm.

The substrate can be any suitable substrate such as glass, or a plastic substrate such as polyethersulfone, polycarbonate, polysulfone, polyethylene terephthalate (PET) and polyethylene naphthalate (PEN). Depending on the design of the organic field effect transistor, the gate electrode, for example highly doped silicon can also function as substrate.

The organic field effect transistor can be prepared by methods known in the art.

For example, a bottom-gate top-contact organic field effect transistor can be prepared as follows: The dielectric material, for example Al$_2$O$_3$ or silicon dioxide, can be applied as a layer on a gate electrode such as highly doped silicon wafer, which also functions as substrate, by a suitable deposition method such as atom layer deposition or thermal evaporation. A self-assembled monolayer of an organic phosphoric acid derivative or an organic silane derivative can be applied to the layer of the dielectric material. For example, the organic phosphoric acid derivative or the organic silane derivative can be applied from solution using solution-deposition techniques. The semiconducting layer can be formed by either solution deposition or thermal evaporation in vacuo of a compound of formula 1 on the self-assembled monolayer of the organic phosphoric acid derivative or the organic silane derivative. Source/drain electrodes can be formed by deposition of a suitable source/drain material, for example tantalum (Ta) and/or gold (Au), on the semiconducting layer through a shadow masks. The channel width (W) is typically 50 μm and the channel length (L) is typically 1000 μm.

Also part of the invention is the use of the compound of formula 1 as semiconducting material.

The compounds of formula 1 show high charge carrier mobility and a high stability, in particular towards oxidation, under ambient conditions. Furthermore the compounds of formula (1) are compatible with liquid processing techniques.

EXAMPLES

Example 1

Preparation of Compound 1a

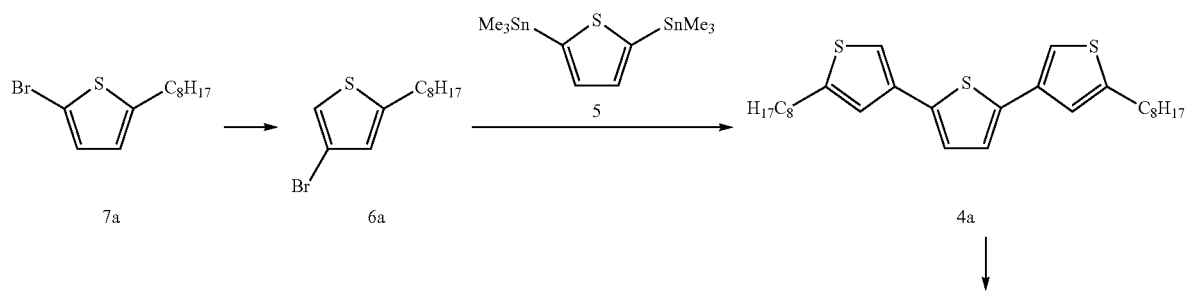

-continued

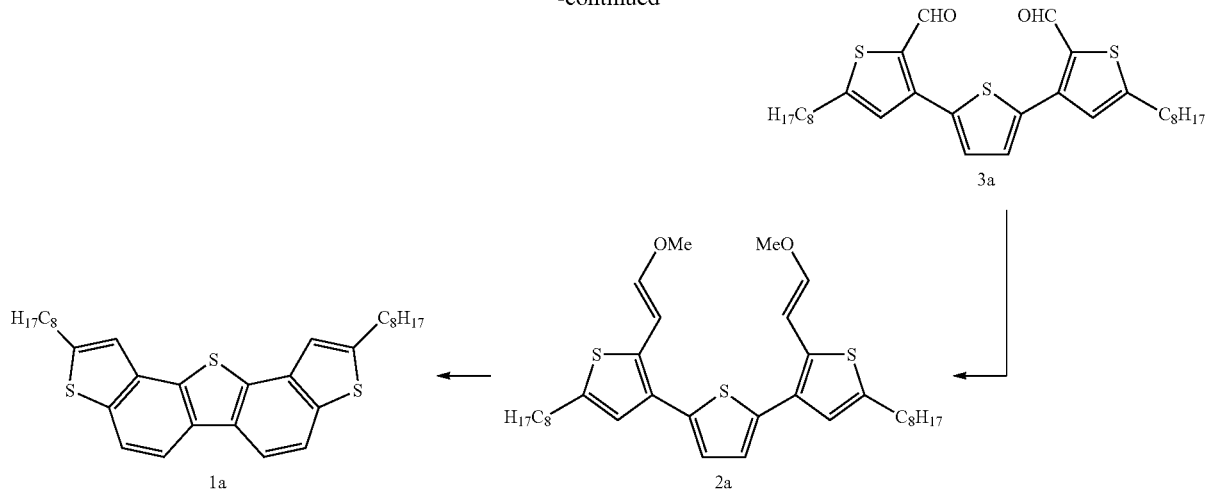

Figure 1:
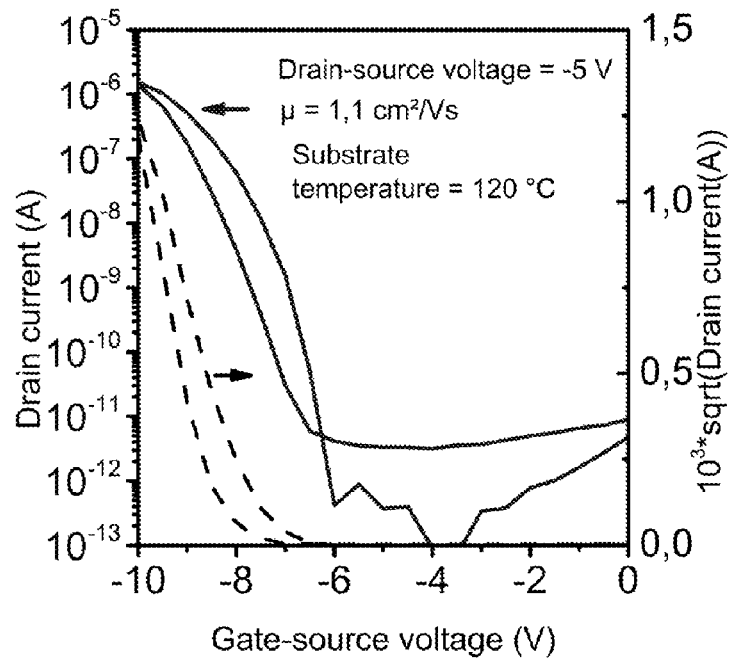
FIG. 1 shows the transfer curve of the OFET of example 6 comprising compound 1a as semiconductor measured at a drain-source voltages V$_d$ of −5V and at temperature of 120° C.

Preparation of Compound 6a:

Commercially available lithium diisopropylamide (LDA) solution (2 M, 34.6 mL, 69.2 mmol) was diluted in THF (350 mL) solution at 0° C. A solution of compound 7a (12.7 g, 46 mmol) in THF (50 mL) was added drop wise to the dilute LDA solution at 0° C. over 60 minutes using a dropping funnel. The resultant mixture was gradually warmed to room temperature and stirred overnight. The reaction mixture was quenched with water (150 mL) and extracted with Et$_2$O (3×100 mL). The combined organic layers were washed with brine and concentrated to give brown oil, which was used purified by column chromatography on silica gel using 100% hexanes to give compound 6a as a yellow oil (10.6 g, 84%). $^1$H NMR (400 MHz, CDCl$_3$) δ 6.99 (s, 1H), 6.70 (s, 1H), 2.77 (t, 2H, J=7.6 Hz), 1.65 (q, 2H, J=8 Hz), 1.34-1.28 (m, 10H), 0.89 (t, 3H, J=6.8 Hz).

Preparation of Compound 4a:

A solution of compound 5 (1.07 g, 2.61 mmol), compound 6a (2.01 g, 7.30 mmol) and Pd(PPh$_3$)$_4$ (0.30 g, 0.26 mmol) were mixed in DMF (13 mL) and stirred at 90° C. for 2 hrs. The resultant suspension was diluted with MeOH (50 mL) and the solids were isolated by vacuum filtration, and washed thoroughly with MeOH (20 mL) followed by hexanes (3×20 mL) to yield compound 4a as a yellow solid (0.92 g, 75%). $^1$H NMR (400 MHz, CDCl$_3$) δ 7.13 (s, 2H), 7.05 (s, 2H), 6.98 (s, 2H), 2.80 (t, 4H, J=7.6 Hz), 1.69 (q, 4H, J=7.2 Hz), 1.38-1.28 (m, 20H), 0.88 (t, 6H, J=7.6 Hz).

Preparation of Compound 3a:

A solution of compound 4a (0.92 g, 1.95 mmol) in CH$_2$Cl$_2$ (15 mL) was added drop wise to a mixture of POCl$_3$ and DMF in CH$_2$Cl$_2$ over 30 minutes at 0° C. The resultant mixture was gradually warmed to room temperature and stirred in a 40° C. hot water bath for 2 hrs. The reaction mixture was diluted with CH$_2$Cl$_2$ and poured into ice (100 mL) and stirred. KOAc (4.2 g) was added portion wise into the cold solution and mixed thoroughly. The organic layer was separated and concentrated to give crude product. The resultant solids were collected by filtration and washed thoroughly with MeOH (3×20 mL) and hexanes (3×20 mL) to yield compound 3a as an orange solid (0.96 g, 93%). $^1$H NMR (400 MHz, CDCl$_3$) δ 10.10 (s, 2H), 7.28 (s, 2H), 7.00 (s, 2H), 2.87 (t, 4H, J=7.8 Hz), 1.73 (m, 4H), 1.40-1.28 (m, 20H), 0.88 (t, 6H, J=7.2 Hz).

Preparation of Compound 2a:

A solution of compound 3a (0.96 g, 1.82 mmol) in THF (33 mL) was added drop wise to a mixture of (methoxymethyl)triphenylphosphonium chloride (3.75 g, 10.94 mmol) and KOtBu (1.23 g, 10.94 mmol) in THF (40 mL) at −50° C. in a dry ice-acetonitrile bath. The resultant mixture was left to stir at this temperature for 5 hours. The reaction mixture was diluted with diethyl ether (100 mL) and brine (100 mL). The organic layer was separated and the aqueous layer further extracted with CH$_2$Cl$_2$ (3×50 mL). Combined organic layers were concentrated and purified by column chromatography on silica gel using hexanes/CH$_2$Cl$_2$ (v/v 1:1) to give compound 2a along with isomers of 2a as a yellow oil (1.0 g, 94%). $^1$H NMR (400 MHz, CDCl$_3$) δ 7.03 (s, 2H), 6.96 (m, 1H), 6.77 (s, 2H), 6.25 (d, 1H, J=11.2 Hz), 6.13 (d, 1H, J=6.4 Hz), 5.98 (m, 1H), 3.83 (s, 3H), 3.68 (s, 3H), 2.76-2.72 (m, 4H), 1.66-1.55 (m, 4H), 1.43-1.27 (m, 20H), 0.87 (t, 6H, J=6.8 Hz).

Preparation of Compound 1a:

The mixture of compound 2a and isomers of compound 2a (1.0 g, 1.71 mmol) obtained in the previous step in CH$_2$Cl$_2$ (30 mL) was treated with methanesulfonic acid (0.05 mL) drop wise at 0° C. in the dark. The resultant mixture was stirred for 16 hrs at room temperature. The reaction mixture was concentrated to dryness and the resultant precipitate triturated with MeOH, then separated by filtration. The residue was washed with methanol and hexane. The crude product was recrystallized from EtOH/CHCl$_3$ to give compound 1a as a yellow solid (0.66 g, 69%). $^1$H NMR (400 MHz, 1,1,2,2-tetrachloroethane-d$_2$) δ 8.06 (d, 2H, J=7.2 Hz), 7.88 (d, 2H, J=8.8 Hz), 7.28 (s, 2H), 3.00 (t, 4H, J=7.6 Hz), 1.82-1.80 (m, 4H), 1.46-1.30 (m, 20H), 0.90 (t, 6H, J=6.8 Hz).

Example 2

Preparation of Compound 1b

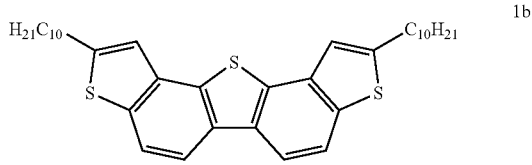

Compound 1b was prepared as white solid in analogy to compound 1a, but starting with compound

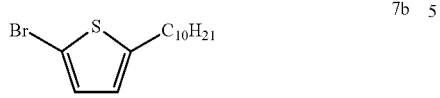

instead of compound 7a.

$^1$H NMR (400 MHz, 1,1,2,2-tetrachloroethane-d$_2$) δ 8.05 (d, 2H, J=8.0 Hz), 7.87 (d, 2H, J=8.0 Hz), 7.28 (s, 2H), 3.00 (t, 4H, J=8.0 Hz), 1.82-1.80 (m, 4H), 1.46-1.27 (m, 29H), 0.88 (t, 6H, J=6.8 Hz).

Example 3

Preparation of Compound 1c

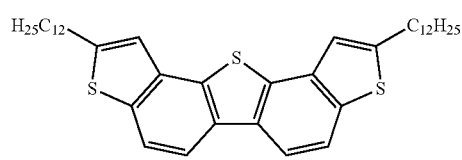

Compound 1c was prepared as white solid in analogy to compound 1a, but starting with compound

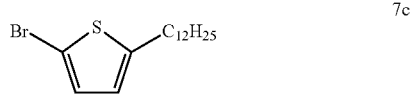

instead of compound 7a.

$^1$H NMR (400 MHz, 1,1,2,2-tetrachloroethane-d$_2$) δ 8.07 (d, 2H, J=8.0 Hz), 7.88 (d, 2H, J=9.2 Hz), 7.28 (s, 2H), 3.00 (t, 4H, J=8.0 Hz), 1.82-1.80 (m, 4H), 1.46-1.27 (m, 36H), 0.88 (t, 6H, J=6.8 Hz).

Example 4

Preparation of compound 1d

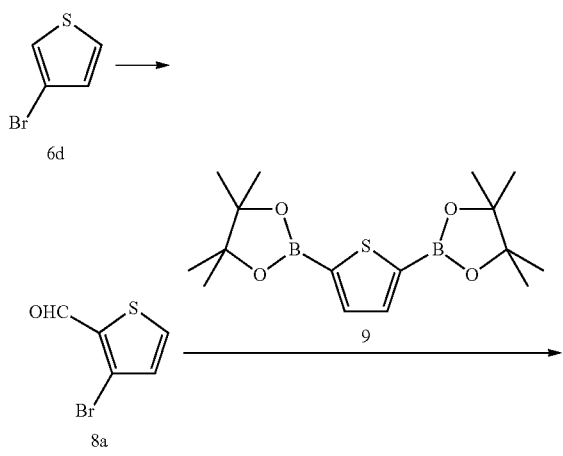

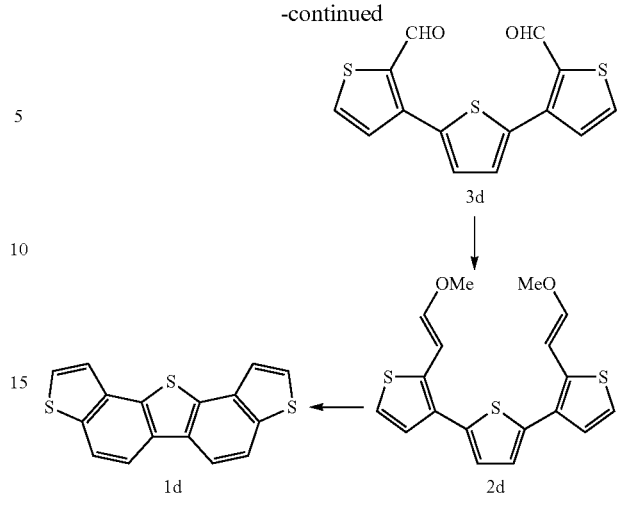

Preparation of Compound 8a:

Commercially available lithium diisopropylamide (LDA) solution (2 M, 27 mL, 53.4 mmol) was diluted in THF (100 mL) solution at 0° C. A solution of compound 6d (5.0 mL, 53.4 mmol) in THF (5 mL) was added drop wise to the dilute LDA solution at 0° C. over 60 minutes using a dropping funnel. The reaction mixture was allowed to stir at 0° C. for 30 minutes. After 30 mins, 1-formyl-piperidine was added drop-wise to the reaction mixture. The resultant mixture was gradually warmed to room temperature and stirred at room temperature for 2 hours. The reaction mixture was quenched with NH$_4$Cl (150 mL) and extracted with Et$_2$O (3×100 mL). The combined organic layers were washed with brine and concentrated to give yellow oil, which was purified by column chromatography on silica gel using DCM: hexane (v/v 1:1) to yield compound 8a as a yellow oil (8.7 g, 85%). $^1$H NMR (400 MHz, CDCl$_3$) δ 9.99 (s, 1H), 7.71 (d, 1H, J=5.2 Hz), 7.15 (d, 1H, J=5.2 Hz).

Preparation of Compound 3d

A solution of compound 9 (2.3 g, 6.92 mmol), compound 8a (2.9 g, 15.23 mmol), CsF (4.2 g, 27.70 mmol) and Pd(PtBu$_3$)$_2$ (70.8 mg, 0.14 mmol) in anhydrous 1,4-dioxane (28 mL) and water (1.1 mL) was stirred at 85° C. for 2 hours. The resultant suspension was diluted with H$_2$O (50 mL) and the solids were isolated by vacuum filtration, and washed thoroughly with MeOH (20 mL) followed by hexanes (3×20 mL) to yield compound 3d as a brown solid (2.02 g, 96%). $^1$H NMR (400 MHz, 1,1,2,2-tetrachloroethane-d$_2$) δ 10.18 (s, 2H), 7.81 (d, 2H, 5.2 Hz), 7.35-7.33 (m, 4H).

Preparation of Compound 2d:

A solution of compound 3d (2.02 g, 6.64 mmol) in THF (30 mL) was added drop wise to a mixture of (methoxymethyl)triphenylphosphonium chloride (13.7 g, 39.85 mmol) and KOtBu (4.5 g, 39.85 mmol) in THF (100 mL) at −50° C. in a dry ice-acetonitrile bath. The resultant mixture was left to stir at this temperature for 5 hours. The reaction mixture was diluted with ethyl acetate (100 mL) and brine (100 mL). The organic layer was separated and the aqueous layer further extracted with ethyl acetate (3×50 mL). Combined organic layers were concentrated and purified by column chromatography on silica gel using hexane/ethyl acetate (v/v 19:1) to give compound 2d along with isomers of compound 2d as brown oil (1.8 g, 76%). $^1$H NMR (400 MHz, CD$_2$Cl$_2$) δ 7.21 (d, 1H, J=5.6 Hz), 7.14-7.02 (m, 5H), 6.30-6.25 (m, 3H), 6.03 (d, 1H, J=6.8 Hz), 3.85 (s, 2H), 3.71 (s, 3H).

Preparation of Compound 1d:

The mixture compound 2d and isomers of compound 2d (1.8 g, 5.02 mmol) obtained in the previous step in CH$_2$Cl$_2$ (80 mL) was treated with methanesulfonic acid (0.05 mL) drop wise at 0° C. in the dark. The resultant mixture was stirred for 16 hours at room temperature. The reaction mixture was concentrated to dryness and the resultant precipitate triturated with MeOH, then separated by filtration. The residue was washed with methanol and hexane to yield compound 1d as a creamy white solid (1.30 g, 87%). $^1$H NMR (400 MHz, 1,1,2,2-tetrachloroethane-d$_2$) δ 8.18 (d, 2H, J=8.4 Hz), 8.02 (d, 2H, J=8.4 Hz), 7.70 (d, 2H, J=5.2 Hz), 7.65 (d, 2H, J=5.2 Hz).

Example 5

Preparation of Compound 1e

1H), 7.16 (m, 1H), 7.00 (s, 1H), 2.85 (t, 2H, J=7.2 Hz), 1.72-1.70 (m, 3H), 1.37-1.27 (m, 13H), 0.89 (m, 3H).

Preparation of Compound 11a:

A solution of compound 10a (112 mg, 0.33 mmol) in anhydrous CH$_2$Cl$_2$ at 0° C. was added N-bromosuccinimide (59.6 mg, 0.33 mmol) followed by acetic acid (1 mL). The resultant mixture was gradually warmed to room temperature and stirred overnight. The reaction mixture was quenched with water and extracted with CH$_2$Cl$_2$ (50 mL×3). The combined organic layer was washed with brine and concentrated to give orange oil, which was purified by column chromatography on silica gel using ethyl acetate/hexane (20/80) to yield compound 11a as orange oil (70 mg, 51%). $^1$H NMR (400 MHz, 1,1,2,2-tetrachloroethane-d$_2$) δ 9.97 (s, 1H), 7.12 (d, 1H, J=3.6 Hz), 7.04 (d, 1H, J=4.0 Hz), 6.93 (s, 1H), 2.84 (t, 2H, J=7.2 Hz), 1.73-1.69 (3H, m), 1.36-1.27 (m, 13H), 0.88 (t, 3H, J=6.8 Hz).

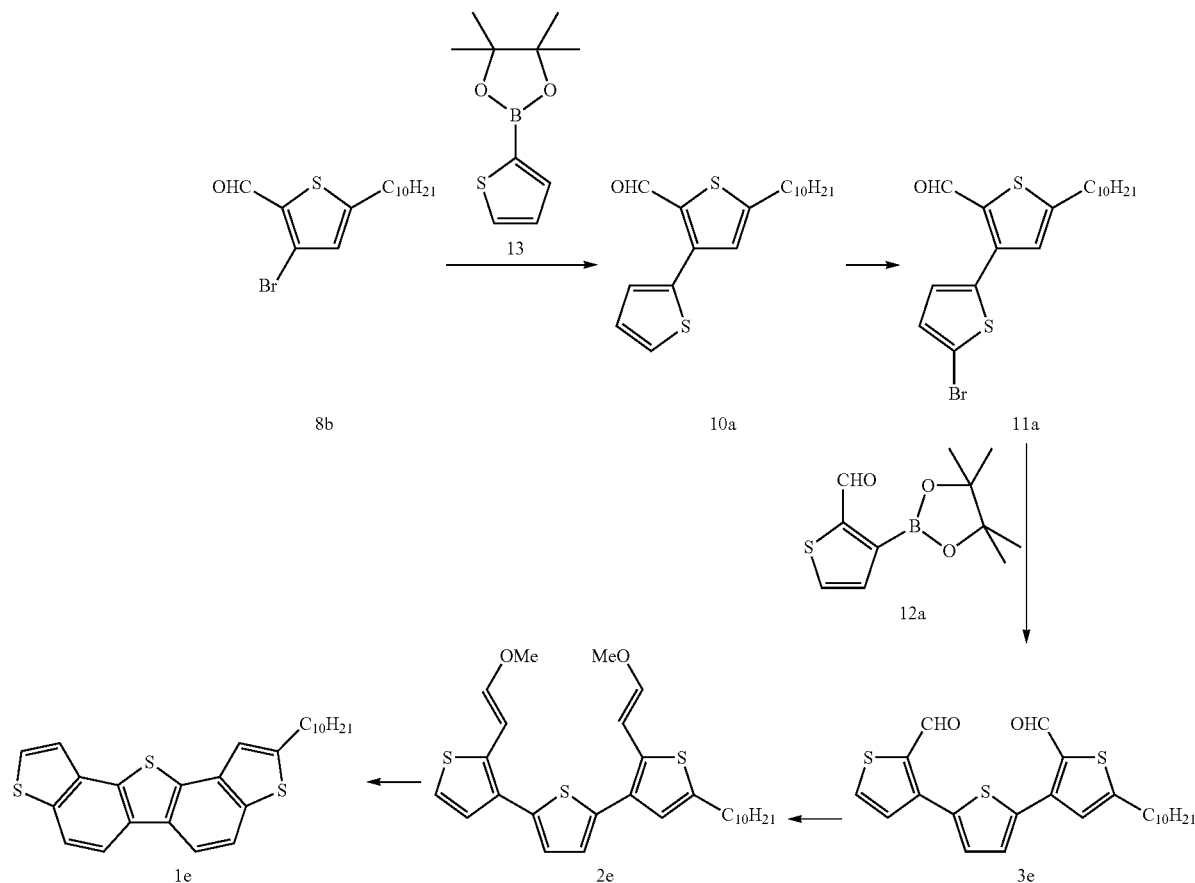

Preparation of Compound 10a:

A solution of compound 13 (697 mg, 3.32 mmol), compound 8b (1.3 g, 3.98 mmol), CsF (2.0 g, 13.27 mmol) and Pd(PtBu$_3$)$_2$ (33.9 mg, 0.07 mmol) in anhydrous 1,4-dioxane (13 mL) and water (0.5 mL) was stirred at 85° C. for 2 hours. The resultant suspension was diluted with H$_2$O (50 mL) and extracted with ethyl acetate (3×50 mL). The combined organic layers was washed with brine and concentrated to give yellow oil, which was purified by column chromatography on silica gel using dichloromethane/hexane (50/50) to yield compound 10a as yellow oil (0.90 g, 81%). $^1$H NMR (400 MHz, CD$_2$Cl$_2$) δ 10.03 (s, 1H), 7.48 (m, 1H), 7.29 (m, Preparation of Compound 3e:

A solution of compound 12a (99.8 mg, 0.42 mmol), compound 11a (173.3 mg, 0.42 mmol), CsF (254.6 mg, 1.68 mmol), Pd(PtBu$_3$)$_2$ (4.3 mg, 0.01 mmol) in anhydrous 1,4-dioxane (4 mL) and water (0.5 mL) was heated at 85° C. for 2 hours. The reaction mixture was quenched with water and extracted with CH$_2$Cl$_2$ (50 mL×3). The combined organic layers were washed with brine and concentrated to give an orange solid, which was purified by column chromatography on silica gel using ethyl acetate/hexane (20/80) to yield compound 3e as orange solid (0.12 g, 66%). $^1$H NMR (400 MHz, 1,1,2,2-tetrachloroethane-d$_2$) δ 10.18 (s, 1H), 10.08 (s, 1H), 7.80 (d, 1H, J=4.8 Hz), 7.34-7.32 (m, 3H), 7.04 (s, 1H), 2.88 (t, 2H, J=6.8 Hz), 1.76-1.72 (m, 3H), 1.40-1.27 (m, 13H), 0.88 (t, 3H, J=5.2 Hz).

Preparation of Compound 2e:

A solution of compound 3e (0.12 g, 0.28 mmol) in THF (5 mL) was added drop wise to a mixture of (methoxymethyl)triphenylphosphonium chloride (0.57 g, 1.67 mmol) and KOtBu (0.19 g, 1.67 mmol) in THF (6 mL) at −50° C. in a dry ice-acetonitrile bath. The resultant mixture was left to stir at this temperature for 5 hours. The reaction mixture was diluted with ethyl acetate (20 mL) and brine (20 mL). The organic layer was separated and the aqueous layer was further extracted with ethyl acetate (3×50 mL). Combined organic layers were concentrated and purified by column chromatography on silica gel using hexanes/ethylacetate (90/10) to give compound 2e along with isomers of compound 2e as yellow oil.

Preparation of Compound 1e:

The mixture of compound 2e and isomers of compound 2e obtained in the previous step (1.8 g, 5.02 mmol) in $CH_2Cl_2$ (80 mL) was treated with methanesulfonic acid (0.05 mL) drop wise at 0° C. in the dark. The resultant mixture was stirred for 16 hours at room temperature. The reaction mixture was concentrated to dryness and the resultant precipitate triturated with MeOH, then separated by filtration. The residue was washed with methanol and hexane to yield compound 1e as a creamy white solid (1.30 g, 87%).

Example 6

Preparation of a Field Effect Transistor Comprising Compound 1a, 1b, Respectively, 1c as Semiconductor Highly doped silicon wafers were coated (30 nm) with $Al_2O_3$ by atom layer deposition and were thoroughly cleaned with acetone and iso-propanol and after a short oxygen plasma treatment functionalized with an octyldecylphosphoric acid monolayer from solution. The highly doped silicon is used as a substrate and back gate electrode, the octyldecylphosphoric acid treated $Al_2O_3$ acts as the gate dielectric. Compound 1a, 1b, respectively, 1c was thermally evaporated in high vacuum while the substrate was held at a defined temperature. Gold source-drain contacts were defined with a shadow mask. The channel width (W) is typically 200 μm and channel length (L) is 100 μm.

Example 7

Preparation of a Field Effect Transistor Comprising Compound 1c as Semiconductors Highly doped p-type silicon (100) wafers with a 200 nm-thick thermally grown silicon dioxide ($SiO_2$) were used as substrates. Prior to deposition of compound 1c the Si/$SiO_2$ surfaces were modified through octyltrichlorosilane (OTS) treatment process. A compound 1c layer was fabricated by solution-deposition technique (chlorobenzene, 1 mg/mL, drop casting at 70° C.). Then a 50 nm-thick Au layer for source and drain electrodes was deposited though a shadow mask to give top-contact OFET devices. The channel width (W) was 1500 μm and channel length (L) was 75 μm.

Example 8

Measurement of the Transfer Curves of the Field Effect Transistors Prepared in Example 6 and 7

The drain current $I_d$ in relation to the gate-source voltage $V_g$ (top transfer curve) and the drain current $I_d^{1/2}$ in relation to the gate-source voltage $V_g$ (bottom transfer curve) of the transistors of examples 6 and 7 were measured on a Keithley 4200 SCS in air at various drain-source voltages $V_d$ and at various temperatures.

FIG. 1 shows the transfer curve of the OFET of example 6 comprising compound 1a as semiconductor measured at a drain-source voltages $V_d$ of −5V and at temperature of 120° C.

Figure 2:
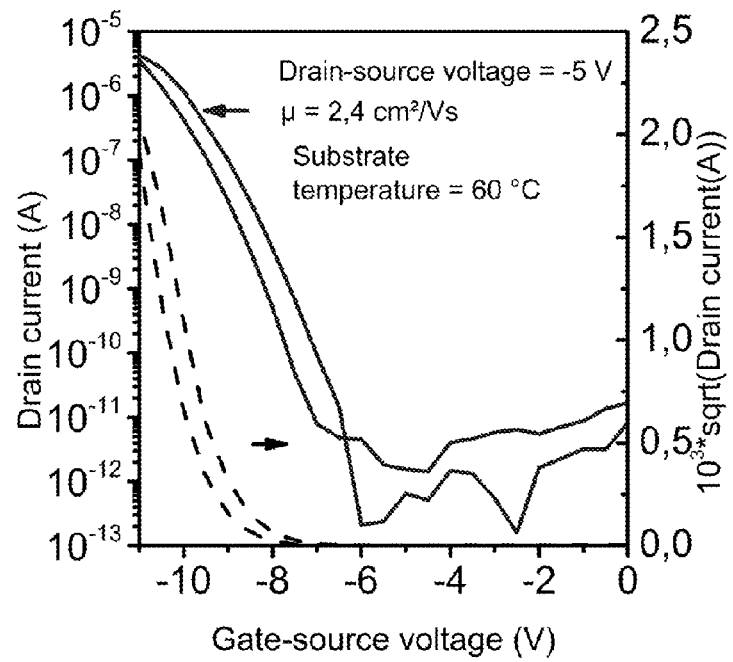
FIG. 2 shows the transfer curve of the OFET of example 6 comprising compound 1c as semiconductor measured at a drain-source voltages V$_d$ of −5V and at temperature of 60° C.

FIG. 2 shows the transfer curve of the OFET of example 6 comprising compound 1c as semiconductor measured at a drain-source voltages $V_d$ of −5V and at temperature of 60° C.

The compounds 1a, 1b and 1c show typical behavior of p-type semiconducting material.

The charge-carrier mobility was extracted in the saturation regime from the slope of the square root drain current $I_d^{1/2}$ versus gate-source voltage $V_g$. The threshold voltage $V_{th}$ was obtained using the following equation: $\mu=2I_d/\{(W/L)Ci\,(V_g-V_{th})^2\}$, wherein Ci is the capacitance of the dielectric layer.

The average values of the charge carrier mobility μ, the $I_{ON}/I_{OFF}$ ratio and the threshold voltage $V_{th}$ for the organic field effect transistor of example 6 comprising compound 1a, 1b and 1c, respectively, and for the organic field effect transistor of example 7 comprising compound 1c as semiconducting material are given in table 1.

TABLE 1

| Example | Semiconductor | $V_{th}$ [V] | μ [$cm^2V^{-1}s^{-1}$] | $I_{on}/I_{off}$ |
|---|---|---|---|---|
| 6 | 1a | −7.6 | 1.1 | 3 × 10$^7$ |
| 6 | 1b | −9 | 0.95 | 6 × 10$^7$ |
| 6 | 1c | −8.9 | 2.2 | 5 × 10$^7$ |
| 7 | 1c | −34 | 0.37 | 1 × 10$^6$ |
| 6 | 1d | −9.0 | 0.027 | 5 × 10$^3$ |
| 6 | 1e | −8.6 | 1.4 | 3 × 10$^7$ |
| 6 | 1e | −9.0 | 2.0 | 6 × 10$^6$ |

The invention claimed is:

1. A compound of formula (I)

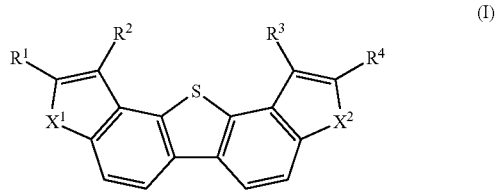

wherein
$X^1$ and $X^2$ are independently O, S, or Se, and
$R^1$, $R^2$, $R^3$ and $R^4$ are independently H, halogen, CN, $NO_2$, a $C_{1-30}$-alkyl, a $C_{2-30}$-alkenyl, a $C_{2-30}$-alkynyl, a $C_{6-14}$-aryl, or a 5 to 14 membered heteroaryl,
wherein
the $C_{1-30}$-alkyl, the $C_{2-30}$-alkenyl and the $C_{2-30}$-alkynyl are optionally substituted by one to five substituents which are independently selected from the group consisting of a $C_{6-10}$-aryl, a 5 to 10 membered heteroaryl, $OR^a$, $OC(O)$—$R^a$, $C(O)$—$OR^a$, $C(O)$—$R^a$, $NR^aR^b$, $NR^a[C(O)R^b]$, $N[C(O)R^a][C(O)R^b]$, halogen, CN and $NO_2$; and one or more $CH_2$-groups, but not adjacent $CH_2$-groups, of the $C_{1-30}$-alkyl, the $C_{2-30}$-alkenyl and the $C_{2-30}$-alkynyl are optionally replaced by O or S, and the $C_{6-14}$-aryl and the 5 to 14 membered heteroaryl are optionally substituted by one to five substituents which are independently selected from the group consisting of a $C_{1-20}$-alkyl, a $C_{2-20}$-alkenyl, a $C_{2-20}$-alkynyl, $OR^a$, $OC(O)-R^a$, $C(O)-OR^a$, $C(O)-R^a$, $NR^aR^b$, $NR^a[C(O)R^b]$, $N[C(O)R^a][C(O)R^b]$, halogen, CN and $NO_2$, wherein $R^a$ and $R^b$ are independently selected from the group consisting of H, a $C_{1-20}$-alkyl, a $C_{2-20}$-alkenyl and a $C_{2-20}$-alkynyl, the $C_{1-20}$-alkyl, the $C_{2-20}$-alkenyl and the $C_{2-20}$-alkynyl are optionally substituted by one to five substituents selected from the group consisting of phenyl, $OR^c$, $OC(O)-R^c$, $C(O)-C(O)-R^c$, $NR^cR^d$, $NR^c[C(O)R^d]$, $N[C(O)R^c][C(O)R^d]$, halogen, CN and $NO_2$, and, the $C_{6-10}$-aryl and the 5 to 10 membered heteroaryl are optionally substituted by one to five substituents independently selected from the group consisting of a $C_{1-10}$-alkyl, a $C_{2-10}$-alkenyl, $C_{2-10}$-alkynyl, $OR^c$, $OC(O)R^c$, $C(O)-OR^c$, $C(O)-R^c$, $NR^cR^d$, $NR^c[C(O)R^d]$, $N[C(O)R^c][C(O)R^d]$, halogen, CN and $NO_2$, wherein $R^c$ and $R^d$ are independently selected from the group consisting of H, a $C_{1-10}$-alkyl, a $C_{2-10}$-alkenyl and a $C_{2-10}$-alkynyl, wherein the $C_{1-10}$-alkyl, the $C_{2-10}$-alkenyl and the $C_{2-10}$-alkynyl are optionally substituted by one to five substituents selected from the group consisting of halogen, CN and $NO_2$.

2. The compound of claim 1, wherein $X^1$ and $X^2$ are independently O or S.

3. The compound of claim 1, wherein $X^1$ and $X^2$ are both S.

4. The compound of claim 1, wherein $R^1$, $R^2$, $R^3$ and $R^4$ are independently H, the $C_{1-30}$-alkyl, the $C_{2-30}$-alkenyl, the $C_{2-30}$-alkynyl, the $C_{6-14}$-aryl or the 5 to 14 membered heteroaryl.

5. The compound of claim 1, wherein $R^1$, $R^2$, $R^3$ and $R^4$ are independently H, the $C_{1-30}$-alkyl, the $C_{6-14}$-aryl or the 5 to 14 membered heteroaryl.

6. The compound of claim 1, wherein $R^2$ and $R^3$ are H, and $R^1$ and $R^4$ are independently H or the $C_{1-30}$-alkyl.

7. The compound of claim 1, wherein $R^2$ and $R^3$ are H, and $R^1$ and $R^4$ are independently H or the $C_{1-30}$-alkyl.

8. An electronic device, comprising the compound of claim 1.

9. The electronic device of claim 8, wherein the electronic device is an organic field effect transistor (OFET).

10. A method for making a semiconductor device, the method comprising incorporating the compound of claim 1 into the semiconductor device as a semiconductor material.

11. A method for conducting a current, the method comprising applying a potential to the compound of claim 1.

\* \* \* \* \*